United States Patent
Giloh et al.

(10) Patent No.: US 9,480,829 B2
(45) Date of Patent: Nov. 1, 2016

(54) ALL DIRECTION STRETCHABLE DRESSING ARTICLE ASSOCIATED WITH CURABLE MATERIALS

(71) Applicant: TamiCare Ltd., Heywood (GB)

(72) Inventors: Ehud Giloh, Heywood (GB); Tamar Giloh, Heywood (GB); Liora Gilboa, Kibutz Kfar Rupin (IL)

(73) Assignee: TamiCare Ltd., Heywood (GB)

( * ) Notice: Subject to any disclaimer, the term of this patent is extended or adjusted under 35 U.S.C. 154(b) by 240 days.

(21) Appl. No.: 13/796,297

(22) Filed: Mar. 12, 2013

(65) Prior Publication Data

US 2014/0200527 A1   Jul. 17, 2014

Related U.S. Application Data

(60) Provisional application No. 61/753,697, filed on Jan. 17, 2013.

(51) Int. Cl.
| | | |
|---|---|---|
| *A61F 13/00* | (2006.01) | |
| *A61M 35/00* | (2006.01) | |
| *A61F 13/10* | (2006.01) | |
| *A61F 13/12* | (2006.01) | |
| *A61K 9/70* | (2006.01) | |

(52) U.S. Cl.
CPC ........ *A61M 35/00* (2013.01); *A61F 13/00038* (2013.01); *A61F 13/10* (2013.01); *A61F 13/12* (2013.01); *A61K 9/70* (2013.01)

(58) Field of Classification Search
CPC ...... A61M 35/00; A61F 13/12; A61F 13/10; A61F 13/00038; A61F 13/00; A61F 2013/0019; A61F 13/0273
USPC .......... 607/96; 604/304–308; 602/74–79, 48, 602/41–43
See application file for complete search history.

(56) References Cited

U.S. PATENT DOCUMENTS

| | | | |
|---|---|---|---|
| 4,230,105 A | * | 10/1980 | Harwood ....................... 604/304 |
| 6,455,610 B1 | * | 9/2002 | Lever ...................... A61L 31/16 523/122 |
| 6,987,210 B1 | | 1/2006 | Giloh |
| 7,354,424 B2 | | 4/2008 | Giloh |
| 7,700,030 B2 | | 4/2010 | Giloh |
| 7,767,133 B2 | | 8/2010 | Giloh et al. |

(Continued)

FOREIGN PATENT DOCUMENTS

| | | |
|---|---|---|
| EP | 1 040 822 A1 | 10/2000 |
| JP | S57-031611 A | 2/1982 |

(Continued)

OTHER PUBLICATIONS

PCT International Search Report and Written Opinion, PCT/IB2014/000540, International Searching Authority, Jun. 30, 2014.

*Primary Examiner* — Kim M Lewis

(74) *Attorney, Agent, or Firm* — McDonnell Boehnen Hulbert & Berghoff LLP

(57) ABSTRACT

An all direction stretchable dressing article is disclosed. The article includes a first surface, a second surface, at least one layer of all directions stretchable polymer, and at least one layer of fibers affixed to at least a part of the polymer layer. The article further includes at least one type of curative material embedded or associated with at least one of the polymer layer or the fiber layer.

10 Claims, 3 Drawing Sheets

(56) References Cited

U.S. PATENT DOCUMENTS

| | | |
|---|---|---|
| 7,901,740 B2 | 3/2011 | Giloh |
| 8,323,764 B2 | 12/2012 | Giloh |
| 2008/0249221 A1* | 10/2008 | Corkery et al. ............. 524/404 |
| 2008/0292788 A1* | 11/2008 | Giloh ...................... B29C 41/08 427/206 |
| 2012/0156427 A1 | 6/2012 | Giloh et al. |
| 2012/0220975 A1* | 8/2012 | Chan et al. ................. 604/384 |
| 2012/0322333 A1 | 12/2012 | Melamed et al. |
| 2013/0017747 A1 | 1/2013 | Giloh |

FOREIGN PATENT DOCUMENTS

| | | |
|---|---|---|
| JP | S59-084815 A | 5/1984 |
| JP | S59-084816 A | 5/1984 |
| WO | 2006084910 A2 | 8/2006 |

\* cited by examiner

ALL DIRECTION STRETCHABLE DRESSING ARTICLE ASSOCIATED WITH CURABLE MATERIALS

CROSS-REFERENCE TO RELATED APPLICATIONS

This application is a non-provisional of U.S. provisional patent application 61/753,697 filed on Jan. 17, 2013, the contents of which are herein incorporated by reference in their entirety.

BACKGROUND

Several nonwoven articles in the market comprise associated materials for skin care etc., for example, Alpha-Arbutin White Mask by DHC. Typical nonwoven materials have some disadvantages such as limited stretchability, limited control over absorption of material in the nonwoven fabric and over the release of the material from the fabric to the wearer skin. The present application seeks to overcome these disadvantages as well as additional advantages.

SUMMARY OF THE INVENTION

An all direction stretchable dressing article comprising embedded or associated curative material and a method of producing such dressing is provided. The dressing article includes at least one layer of all direction stretchable polymer, at least one layer of fibers affixed to at least a part of the polymer layer, and at least one type of curative material embedded in or associated with at least one of the at least two layers.

In one embodiment, the all direction stretchable dressing article includes at least one layer of an all direction stretchable polymer having a first surface and a second surface, fibers or loose fibers affixed to at least part of one of the first surface, the second surface, or both of the dressing article, and curative materials embedded in or associated with at least a part of the polymer layer, the fibers, or both of said all direction stretchable dressing article. The curative materials are readily active in a wet or a dry appearance or activated at any desired time by applying any suitable effect or energy, or by adding any suitable material in any form, and the polymer layer is considerably impermeable to keep the curative materials attached to the wearer's skin or to the first surface of the dressing only with no leakage from one side of the dressing to the other.

The polymer layer may have different shapes, thicknesses, material composition, colors, scents, patterns or printing, as well as holes, perforations, and embossing at different areas. The fibers may be loose fibers of at least one type, super absorbent fibers, or any other suitable type of fibers.

At least one curative material is applied to the article during the article manufacturing process at any stage, or after the manufacturing process.

DETAILED DESCRIPTION

Figure 1:
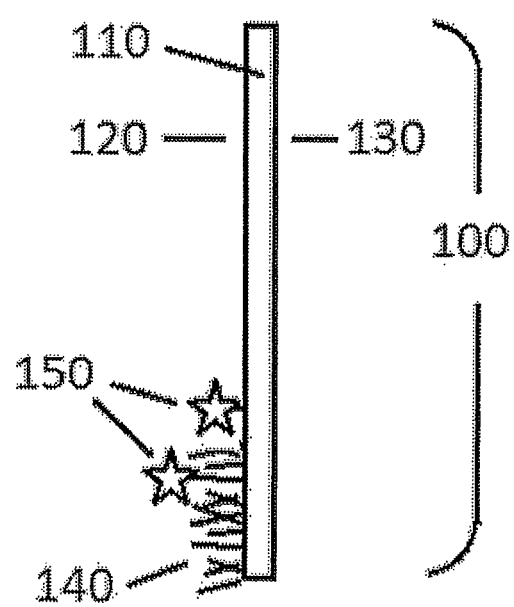
FIG. 1 illustrates a representative all direction stretchable dressing article 100 including a layer 110 of an all direction stretchable polymer having a first surface 120 and a second surface 130, fibers 140 affixed to the first surface 120, a curative material 150 associated with first surface 120 and fibers 140.
Figure 2:
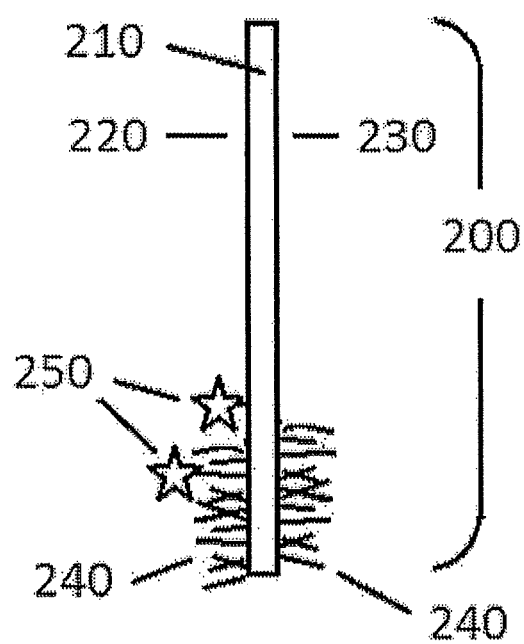
FIG. 2 illustrates a representative all direction stretchable dressing article 200 including a layer 210 of an all direction stretchable polymer having a first surface 220 and a second surface 230, fibers 240 affixed to the first surface 220 and second surface 230, a curative material 250 associated with first surface 220 and fibers 230.
Figure 3:
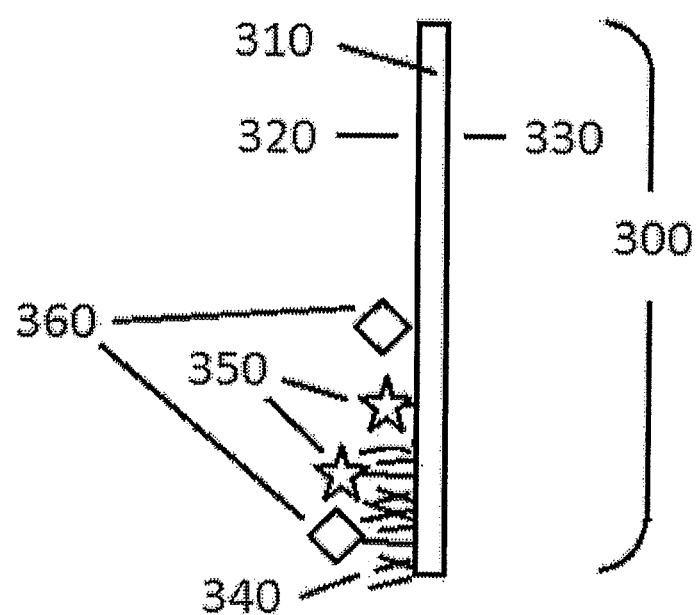
FIG. 3 illustrates a representative all direction stretchable dressing article 300 including a layer 310 of an all direction stretchable polymer having a first surface 320 and a second surface 330; fibers 340 affixed to the first surface 320; and a first curative material 350 and a second curative material 360 associated with the first surface 320.

An all direction stretchable dressing article having at least two surfaces is provided. The dressing article includes at least one layer of all directions stretchable polymer such as, but not limited to, natural or artificial rubber, such as latex, neoprene, or any other suitable elastomeric material, such as the material described in U.S. Pat. Nos. 7,767,133, 7,901,740, and 8,323,764, which are hereby incorporated by reference in their entireties. The layer may have different shapes, thicknesses, material composition, colors, scents, patterns or printing, as well as holes, perforations, and embossing at different areas. Example shapes for the layer are described in U.S. Pat. No. 7,700,030, which is hereby incorporated by reference in its entirety.

Fibers or loose fibers of at least one type such as, but not limited to, cotton, viscose, polypropylene, polyethylene, or any other suitable fiber type are affixed to at least part of one surface of the dressing article. The fibers may be of different thicknesses, lengths, colors etc., and may have different dedicated performances qualities, such as but not limited to, liquid absorption, liquid repulsion, or any other desired properties and combinations. Additional examples of loose fibers are described in U.S. Pat. Nos. 7,767,133, 7,901,740, and 8,323,764, which are hereby incorporated by reference in their entireties.

Curative materials are embedded in or associated with at least a part of one surface of the all direction stretchable dressing article. The curative materials may be embedded into or associated with at least one of the at least two layers. The curative materials may be applied during the dressing article manufacturing process at any stage, or may be applied after the manufacturing process.

In this application the term 'curative' may refer to any medical materials, such as, but not limited to, antibacterial, chemotherapy, sedative and other curative materials, nano particles, cosmetic materials, such as, but not limited to, anti-aging, facials, and creams for acne treatments and other cosmetic materials, therapeutic materials such as, but not limited to, burn treatments, esthetic surgeries treatments, anti-fungal etc., physical, mental, or emotional treatments such as, but not limited to, antiperspirants, good feel scents, and aroma therapy materials, or any material that may affect the user of the product or an individual being in physical contact with the user of the product.

The curative materials may be readily active in a wet or a dry appearance, or may be activated at any desired time by applying any suitable effect or energy, such as but not limited to, heat, light, pressure, noise, vibrations, radiation, laser, ultrasound, electricity or any other appearance of energy or physical effect or by adding any suitable material in any form, such as but not limited to any liquid, powder, steam, and the like.

The polymeric layer, being considerably impermeable, keeps the curative materials attached to the wearer skin or to the outer surface of the dressing only, with no leakage from one surface of the dressing fabric to the other surface.

In one embodiment, the stretchable dressing article may form a sleeve shape.

In another embodiment, the stretchable dressing article may form an enclosed space such as a glove, a sock, a full head mask, etc.

In yet another embodiment, the stretchable dressing may be constructed as a sheet or strap.

In yet another embodiment, the stretchable dressing may have at least one additional hole or opening which may be supported by body parts such as, but not limited to, the nose, mouth, ears, fingers, and/or toes, etc., so that the body parts protrude through the openings, and so that only the intended body parts are covered.

In yet another embodiment, the curative material is applied on the outer surface of the dressing to cause a desired effect such as antiseptic protection.

In yet another embodiment, more than one curative material is embedded to or attached to the surface of the dressing. For, example one part of the fibers may comprise antiperspirant and a second part of the fibers may comprise an anti-ageing material.

In yet another embodiment, the dressing article applies constant slight pressure on the wearer's skin or body promoting the usefulness of the curative materials effect.

In yet another embodiment, the polymeric layer, being considerably impermeable, keeps the curative materials attached to the wearer's skin.

In yet another embodiment, nanometric particles are used in various ways, such as, for example, to amplify the effect of another curative material.

In yet another embodiment, the fibers are covered by a top sheet. The top sheet may stay during usage or be removed in order to expose the curative material to direct contact with the wearer's skin. Top sheets can be of any suitable materials, including without limitation, non-woven porous polymeric films or membranes.

The invention claimed is:

1. An all direction stretchable, non-woven, shaped dressing article comprising:
  (a) at least one layer of an all direction stretchable polymer having a first surface and a second surface, the stretchable polymer is a member selected from the group consisting of natural rubber, artificial rubber, or an elastomeric material;
  (b) loose fibers directly affixed to at least part of one of the first surface, the second surface, or both the first and second surfaces of the polymer layer of the all direction stretchable dressing article; and
  (c) curative materials embedded in or associated with at least a part of the polymer layer, the fibers, or both of said all direction stretchable dressing article,
  wherein the curative materials are readily active in a wet or a dry appearance or activated at any desired time,
  wherein the polymer layer is capable of maintaining the curative materials against the wearer's skin without leakage through the polymer layer,
  wherein the dressing article is shaped such that polymer layer is capable of applying constant pressure against the wearer's skin to promote the effect of the curative materials, and
  wherein part of the fibers comprises the curative material and a remaining part of the fibers comprises a different curative material.

2. An all direction stretchable, non-woven, shaped dressing article comprising:
  (a) at least one layer of an all direction stretchable polymer having a first surface and a second surface, the stretchable polymer is a member selected from the group consisting of natural rubber, artificial rubber, or an elastomeric material;
  (b) loose fibers directly affixed to at least part of one of the first surface, the second surface, or both the first and second surfaces of the polymer layer of the all direction stretchable dressing article; and
  (c) curative materials embedded in or associated with at least a part of the polymer layer, the fibers, or both of said all direction stretchable dressing article,
  wherein the curative materials are readily active in a wet or a dry appearance or activated at any desired time,
  wherein the polymer layer is capable of maintaining the curative materials against the wearer's skin without leakage through the polymer layer,
  wherein the dressing article is shaped such that polymer layer is capable of applying constant pressure against the wearer's skin to promote the effect of the curative materials, and
  wherein the polymer layer comprises the curative material and the fibers comprises a different curative material.

3. An all direction stretchable, non-woven, shaped dressing article comprising:
  (a) at least one layer of an all direction stretchable polymer having a first surface and a second surface, the stretchable polymer is a member selected from the group consisting of natural rubber, artificial rubber, or an elastomeric material;
  (b) loose fibers directly affixed to at least part of one of the first surface, the second surface, or both the first and second surfaces of the polymer layer of the all direction stretchable dressing article; and
  (c) curative materials embedded in or associated with at least a part of the polymer layer, the fibers, or both of said all direction stretchable dressing article,
  wherein the curative materials are readily active in a wet or a dry appearance or activated at any desired time,
  wherein the polymer layer is capable of maintaining the curative materials against the wearer's skin without leakage through the polymer layer,
  wherein the dressing article is shaped such that polymer layer is capable of applying constant pressure against the wearer's skin to promote the effect of the curative materials, and
  wherein the polymer layer comprises the curative material, part of the fibers comprises a second curative material, and a remaining part of the fibers comprises a third curative material.

4. The all direction stretchable, non-woven, shaped dressing article according to any one of claims 1, 2, or 3, wherein the curative materials are activated by one or more of heat, light, pressure, noise, vibrations, radiation, laser, or ultrasound.

5. The all direction stretchable, non-woven, shaped dressing article according to any one of claims 1, 2, or 3, wherein the curative materials are activated by adding one or more of a liquid, powder, or steam.

6. The all direction stretchable, non-woven, shaped dressing article according to any one of claims 1, 2, or 3, wherein the article forms a sleeve shape having at least two openings.

7. The all direction stretchable, non-woven, shaped dressing article according to any one of claims 1, 2, or 3, wherein the article is forms an enclosed space having one opening.

8. The all direction stretchable, non-woven, shaped dressing article according to claim 7, wherein the article is a glove, a sock, or a full head mask.

9. The all direction stretchable, non-woven, shaped dressing article according to any one of claims 1, 2, or 3, wherein the article is constructed as a sheet or strap.

10. The all direction stretchable, non-woven, shaped dressing article according to any one of claims 1, 2, or 3, further comprising a top sheet covering the fibers.

* * * * *